US00PP20274P2

(12) United States Plant Patent
Delabroye

(10) Patent No.: US PP20,274 P2
(45) Date of Patent: Sep. 8, 2009

(54) ***HEUCHERA* PLANT NAMED 'MIRACLE'**

(50) Latin Name: ***Heuchera* hybrid**
Varietal Denomination: Miracle

(76) Inventor: Sandrine Delabroye, Rue Roger Salengro 40, F-59496 Hantay (FR)

( * ) Notice: Subject to any disclaimer, the term of this patent is extended or adjusted under 35 U.S.C. 154(b) by 0 days.

(21) Appl. No.: 12/218,823

(22) Filed: Jul. 18, 2008

(51) Int. Cl.
*A01H 5/00* (2006.01)

(52) U.S. Cl. ..... Plt./440

(58) Field of Classification Search ..... Plt./440
See application file for complete search history.

*Primary Examiner*—June Hwu
(74) *Attorney, Agent, or Firm*—Penny J. Aguirre

(57) ABSTRACT

A new cultivar of *Heuchera* of hybrid origin, 'Miracle', that is characterized by its small to medium sized, ruffled, ovate-shaped leaves with unique coloration that changes throughout the growing season. In the spring and fall with cool temperatures, the leaves have red mottled centers with yellow-green margins and veins. In the summer, the leaves become greener with a silvery overlay. 'Miracle' is further characterized by its mounded and compact plant habit, its hardiness at least in U.S.D.A Zones 4 to 9, its tolerance to heat and humidity, its vigorous growth habit, and its spikes of pink flowers in late spring to early summer.

2 Drawing Sheets

Botanical classification: *Heuchera* hybrid.
Cultivar designation: 'Miracle'.

CROSS REFERENCE TO A RELATED APPLICATION

This application is co-pending with U.S. Plant Patent applications filed for sibling plants derived from the same cross in the inventor's breeding program that are entitled *Heuchera* Plant Named 'Beaujolais' (U.S. Plant Pat. No. 19,577), *Heuchera* Plant Named 'Encore' ((U.S. Plant Pat. No. 19,578), *Heuchera* Plant Named 'Pinot Gris' (U.S. Plant Pat. No. 19,592), *Heuchera* Plant Named 'Pinot Noir' (U.S. Plant patent application Ser. No. 12/002,889), *Heuchera* 'Tiramisu' (U.S. Plant patent application Ser. No. 12/002, 921) and *Heuchera* Plant Named 'Pistache' (U.S. Plant Pat. No. 19,585).

BACKGROUND OF THE INVENTION

The present invention relates to a new and distinct cultivar of hybrid *Heuchera*, botanically known as a *Heuchera* of hybrid origin and is hereinafter referred to by the cultivar name 'Miracle'.

The new cultivar was derived from a controlled breeding program by the inventor in Hantay, France. The inventor made a cross in summer of 2005 between *Heuchera* 'Gloire d'Orleans' (not patented, syn. *Heuchera*×*brizoides* 'Gloire d'Orleans') and *Heuchera*×*villosa* 'Caramel' (U.S. Plant Pat. No. 16,560). The goal of the breeding program was to obtain unique cultivars of *Heuchera* that combined the flowering habit of 'Gloire d'Orleans' with the vigor and unique foliage coloration of *Heuchera*×*villosa*. The inventor selected 'Miracle' in 2007 as a single unique plant amongst the seedlings that resulted from the above cross.

Asexual reproduction of the new cultivar was first accomplished under direction of the inventor by in vitro propagation in Rijswijk, The Netherlands in winter of 2007. Asexual reproduction of the new cultivar by division and tissue culture has shown that the unique features are stable and reproduced true to type in successive generations.

SUMMARY OF THE INVENTION

The following traits have been repeatedly observed and represent the characteristics of the new cultivar. These attributes in combination distinguish 'Miracle' as a new and unique cultivar of *Heuchera*.

1. 'Miracle' exhibits uniquely colored foliage with leaves that changes coloration throughout the season and with the temperature of the growing conditions. In the spring, the leaves are yellow-green with centers mottled with red with yellow-green margins and veins. In the summer, the leaves become green with a silvery overlay. In the fall with cool temperatures, the leaves once again develop red mottled centers with yellow-green margins and veins.
2. 'Miracle' exhibits medium to small sized, somewhat ruffled, ovate shaped leaves.
3. 'Miracle' exhibits a mounded and compact plant habit.
4. 'Miracle' is hardy in at least U.S.D.A. Zones 4 to 9.
5. 'Miracle' exhibits a vigorous growth habit.
6. 'Miracle' exhibits tolerant to heat and humidity.
7. 'Miracle' exhibits compound spikes of pink flowers in late spring to early summer.

'Miracle' is a unique *Heuchera* with foliage coloration that is unknown to exist in other cultivars of *Heuchera* known to the inventor. 'Miracle' differs from its parent plants in that 'Caramel' is a ×*villosa* hybrid and has foliage that is more orange in color and lacks red mottling and Gloire d'Orleans is a ×*brizoides* hybrid with green foliage.

'Miracle' can be compared most closely compared to its sibling, 'Tiramisu', for its similar leaf form and coloration, however 'Miracle' differs in having smaller more ruffled leaves, leaves that become more green in summer (less yellow), in having a more vigorous growth habit and in having pink flowers rather than white. The closest comparison plants in overall leaf shape, habit, and performance are other sibling cultivars that differ in foliage coloration; 'Beaujolais' has burgundy-red leaves overlaid with silver, 'Encore' has rose-purple leaves, 'Pinot Gris' has leaves that emerge orange-yellow and mature to a rose color with a silvery overlay, 'Pinot Noir' has dark purple-gray leaves with a silver overlay, and 'Pistache' has yellow-green leaves.

BRIEF DESCRIPTION OF THE DRAWING

The accompanying colored photographs illustrate the overall appearance and distinct characteristics of the new *Heuchera*. The photographs were taken of two year-old plants as grown outdoors in two-gallon containers in the inventor's nursery in Hantay, France.

The photograph in FIG. 1 provides a side view of a plant of 'Miracle' and depicts foliage coloration that is typical in spring.

Figure 1:
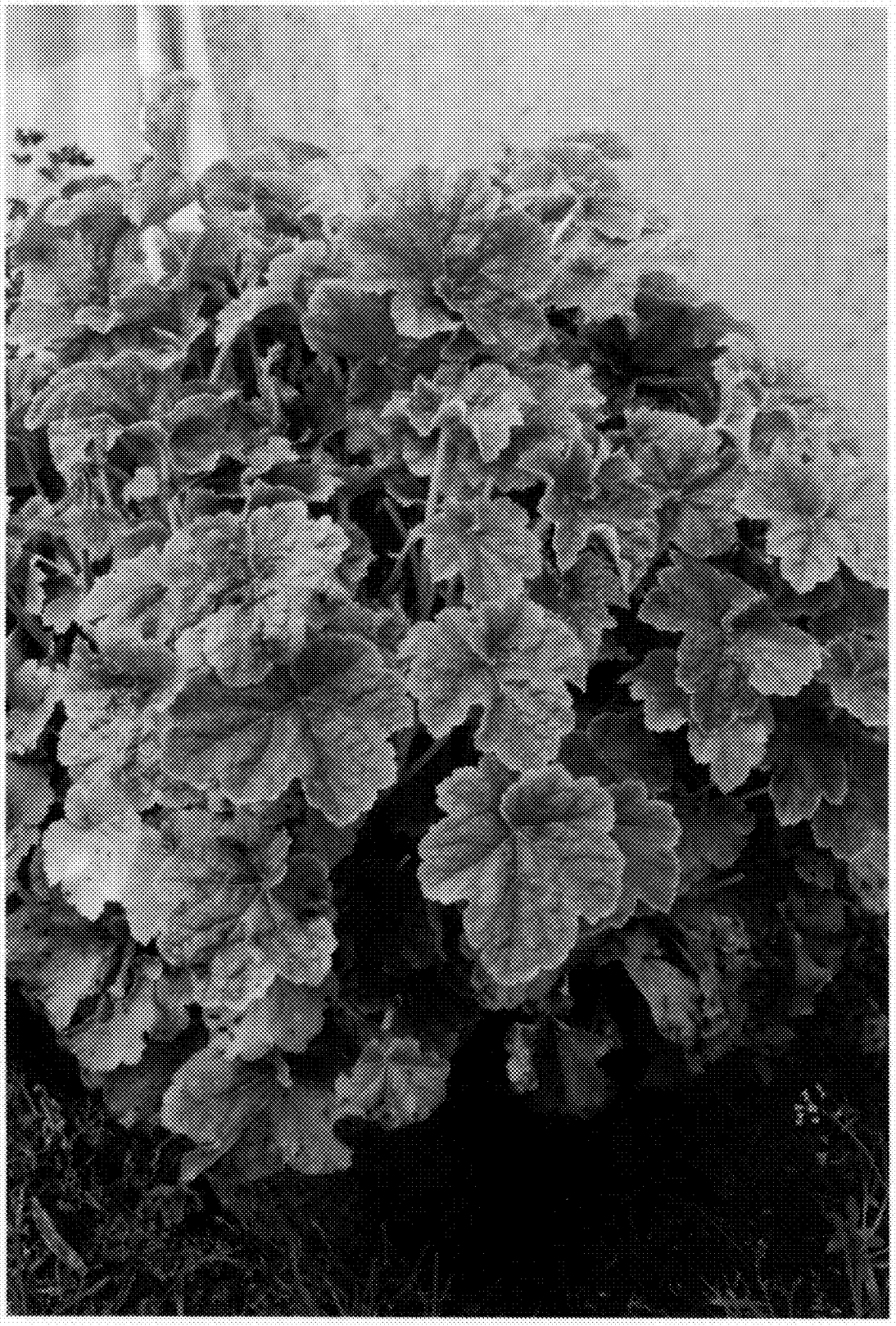
Figure 2:
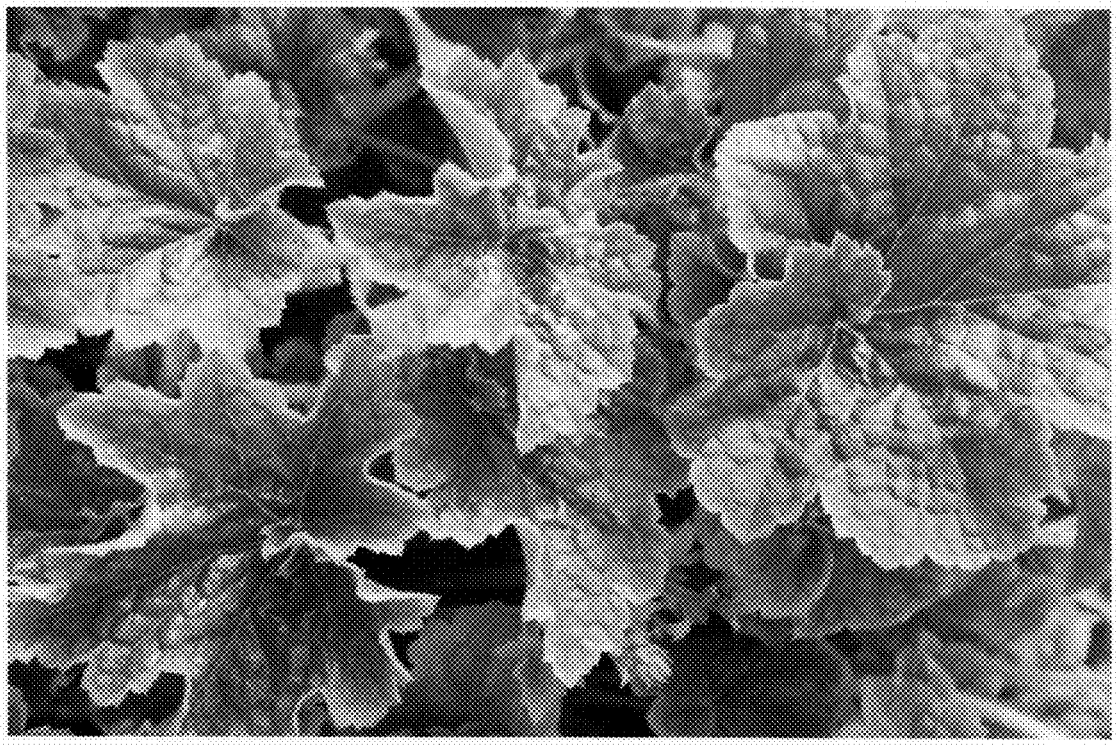

The photograph in FIG. 2 provides a close-up view of the spring foliage of 'Miracle' with the lower leaves changing over to its summer coloration.

Figure 3:
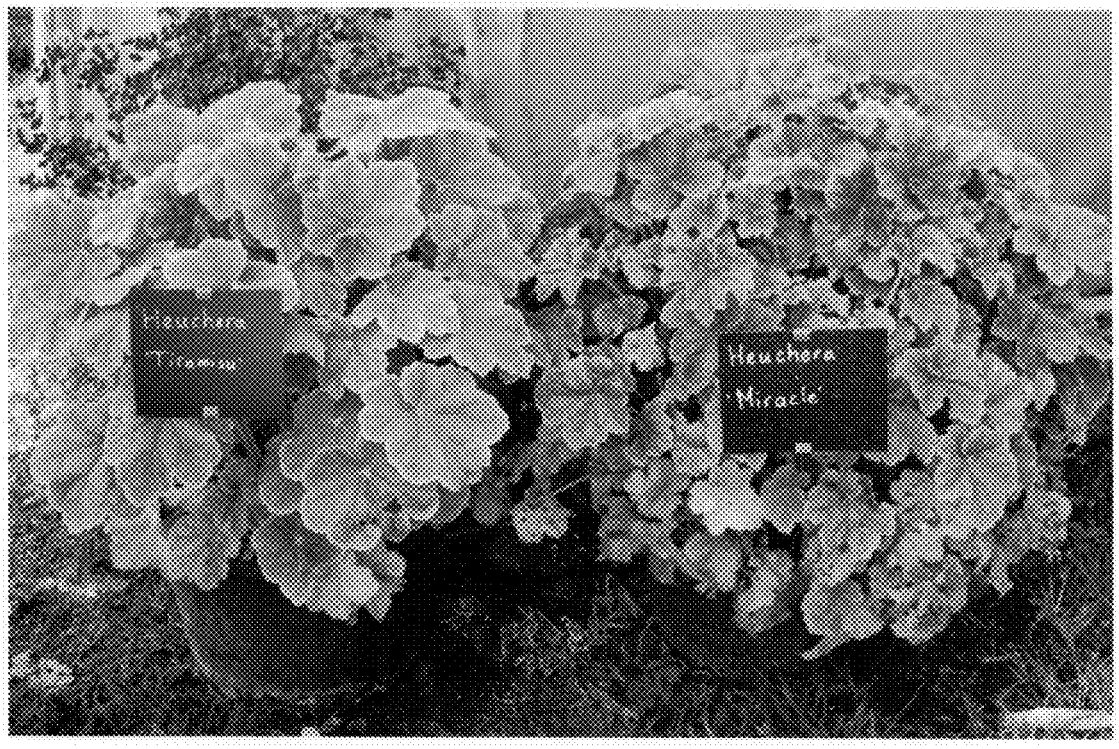

The photograph in FIG. 3 provides a comparison between 'Tiramisu' (left) and 'Miracle' (right).

The colors in the photographs are as close as possible with the photographic and printing technology utilized. The color values cited in the detailed botanical description accurately describe the colors of the new *Heuchera*.

DETAILED BOTANICAL DESCRIPTION OF THE PLANT

The following is a detailed description of a 6 month-old plants of the new cultivar as grown with 2 plants in a 5-liter containers outdoors in The Netherlands. The plants were grown under average day temperatures of 10° to 25° C. and average night temperatures of 3° to 14° C. The phenotype of the new cultivar may vary with variations in environmental, climatic, and cultural conditions, as it has not been tested under all possible environmental conditions. The color determination is in accordance with the 2001 R.H.S. Colour Chart of The Royal Horticultural Society, London, England, except where general color terms of ordinary dictionary significance are used.

General description:

*Plant habit.*—Compact, clump-forming herbaceous perennial, mounded foliage.

*Height and spread.*—Reaches about a height of about 12 cm in height (30 cm in bloom) and about 20 cm in width in a 5-liter container.

*Blooming period.*—Late spring to early summer.

*Hardiness.*—U.S.D.A. Zones 4 to 9.

*Culture.*—Full sun to medium shade in moist, well-drained, fertile soils with tolerance to heat and humidity.

*Diseases and pests.*—Disease free in the conditions tested, no susceptibility or resistance to pests has been observed.

*Root description.*—Fibrous roots on woody rootstalks.

*Branching habit.*—Basal rosettes of leaves on petioles.

*Propagation.*—In vitro propagation is the preferred method.

*Root initiation.*—Roots appear in rooting media in 10 days at 20° C. in the laboratory without supplemental lighting.

*Root development.*—Rooted transplants from tissue culture fully develop at least a 9 cm container in about 20 weeks in a greenhouse with average temperatures of about 20° C. without supplemental lighting in The Netherlands.

*Growth rate.*—Vigorous relative to most *Heuchera* cultivars.

Foliage description:

*Leaf shape.*—Broadly ovate.

*Leaf division.*—Simple.

*Leaf base.*—Hastate, moderately overlapping.

*Leaf apex.*—Abruptly acute.

*Leaf venation.*—Laciniate, conspicuous on spring and fall foliage with upper surface N144B in color and lower surface 145C in color.

*Leaf margins.*—Lobed with average of 7 lobes per leaf, lobe margins crenate.

*Leaf attachment.*—Petiolate.

*Leaf arrangement.*—Basal rosettes.

*Leaf orientation.*—Held horizontal to petiole, ruffled.

*Leaf surface.*—Dull on upper and lower surface and slightly rough to touch; upper and lower surface is very sparsely covered with hairs about 0.5 mm in length and 155C in color.

*Leaf color.*—Upper surface, spring and fall; N144C with mottling on leaf centers of 166B to 174B with blotches near margins and veins 151A to 151 C and margins N144C, lower surface, spring and fall; 177D with blotches near margins and veins 145A to 145B, upper surface, summer; changes to 144B to 145A with small darker blotches near main veins in center 152B to 152D, lower surface, summer; changes to 145A to 145B with small darker blotches near main veins in center 152D.

*Leaf size.*—Average of 7 cm in length and 6.2 cm in width.

*Leaf quantity.*—Average of 65 per 5-liter container.

*Petioles.*—Round in shape, average length of 9.5 cm; average diameter of 3 mm, 145A to 145B in color with base tinged 182B to 182D, surface is glabrous.

*Stipules.*—None.

Flower description:

*Inflorescence type.*—Numerous small bell-shaped flowers arranged on pyramidal panicles on flower scapes emerging from the base of the rosette, each peduncle has 2 pairs of lateral thryses and a terminal flower (compound spikes).

*Inflorescence size.*—Reaches an average of 30 cm in height and about 4 cm in width in full bloom.

*Flower fragrance.*—None.

*Flower quantity.*—Average of 60 flowers per inflorescence.

*Flower lastingness.*—Average of 7 days per flower, individual panicles bloom for about 3 weeks, flowers self cleaning.

*Flower buds.*—Broadly elliptic to slightly obovate, average of 2.5 mm in diameter and 4 mm in depth, color is 62C to 62D flushed with 146D and basal portion 144C.

*Flower aspect.*—Held slightly downward (drooping) on pedicels held at about a 45° angle from peduncle.

*Flower shape.*—Campanulate, with base implanted in hypanthium where sepals, petals and filaments are fused.

*Flower size.*—Average of 6 mm in diameter and depth.

*Petals.*—About 5, narrowly elliptic in shape and emerge from between sepals in hypanthium, margin is entire, apex is narrowly apiculate, about 4 mm in length and 0.8 mm in width, upper and lower surface is glabrous and dull, color of upper and lower surface when opening is 62D, color of upper and lower surface when fully open is a color between 62D and N155B, color of both surfaces fades to N155B.

*Calyx.*—Campanulate, sepals fused in hypanthium, 6 mm in diameter and 5 mm in depth.

*Sepals.*—5, unfused portion is broadly oblong in shape, average of 5 mm in length and 2.5 mm in width, margin is entire, apex is broadly acute, base is fused, surface very villose, color of upper surface when opening; 62C with base 144C, color of lower surface when opening; 62C flushed with 146D with base 144C, color of upper surface when fully open; 62C to 63D with base 144C, color of lower surface when opening; 62C flushed with 144C with base 146A to 146B.

*Rachis* (*flower scape*).—Average of 29.5 cm in length and 1.5 mm in width, color is 152A to 152B, surface is pilose, held at about a 15° angle from vertical.

*Peduncles.*—Average of 1.3 cm in length and of 0.5 mm in width, pilose surface, 152A to 152B in color, held at about a 80° angle from vertical.

*Pedicels.*—Average of 4 mm in length and about 0.5 mm in width, pilose surface, 152A to 152B in color, held at about a 45° angle to peduncle.

*Gynoecium.*—2 Pistils, club-shaped, about 4 mm in length, stigmas minute and 157D in color, styles are continuous with superior ovary, about 3.5 mm in length and 157B to 157C in color, ovary is 144C in color.

*Androcoecium.*—Average of 5 stamens, anthers are ovate in shape, basifixed, about 0.4 mm in length and 64A in color, filaments are about 0.6 mm in length and N155B to N155C in color, no pollen was detected.

*Seed.*—Seed development of the new cultivar has not been observed.

It is claimed:

1. A new and distinct cultivar of *Heuchera* plant named 'Miracle' as herein illustrated and described.

* * * * *